United States Patent [19]

Wong

[11] Patent Number: 5,798,696
[45] Date of Patent: Aug. 25, 1998

[54] TIRE PUNCTURE LOCATOR

[75] Inventor: Jacob Y. Wong, Goleta, Calif.

[73] Assignee: Jaesent Inc., Goleta, Calif.

[21] Appl. No.: 855,174

[22] Filed: May 13, 1997

[51] Int. Cl.[6] .................................................. G08B 21/00
[52] U.S. Cl. ........................... 340/605; 340/442; 73/40; 73/40.7; 73/49
[58] Field of Search ................................ 340/605, 442; 73/40, 40.7, 49

[56] References Cited

U.S. PATENT DOCUMENTS 4,693,118  9/1987  Roberts ........................... 73/40.7

4,754,638  7/1988  Brayman et al. ................. 73/40.7

*Primary Examiner*—Edward Lefkowitz
*Attorney, Agent, or Firm*—Daniel C. McKown

[57] ABSTRACT

Apparatus for detecting leaks in pneumatic tires includes a source of pressurized carbon dioxide gas that is used to partially re-inflate the flat tire, so that a strong concentration of carbon dioxide gas will be present in any gas that leaks out of the tire. In the vicinity of the leak, the concentration of carbon dioxide gas is greatly enhanced above the normal atmospheric concentration of 300 to 800 parts per million. The enhanced concentration of carbon dioxide gas in the vicinity of the leak is detected by a gas sampling system that includes an audible alarm that alerts the user when the location of the leak has been found.

8 Claims, 2 Drawing Sheets

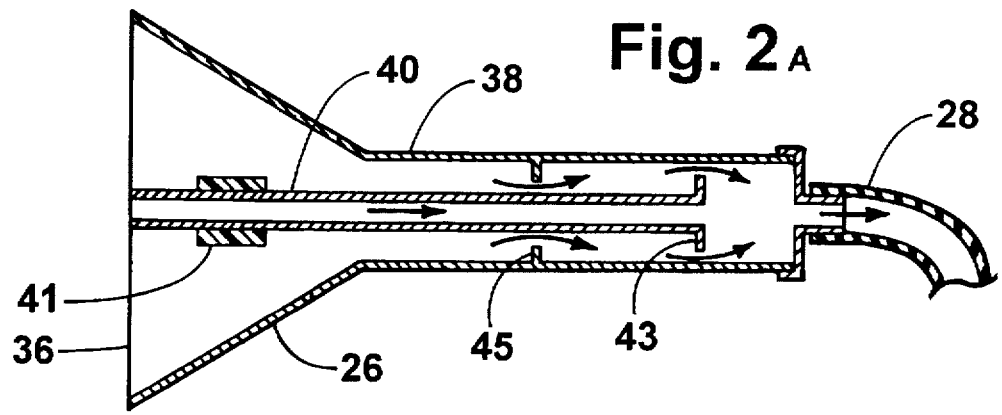
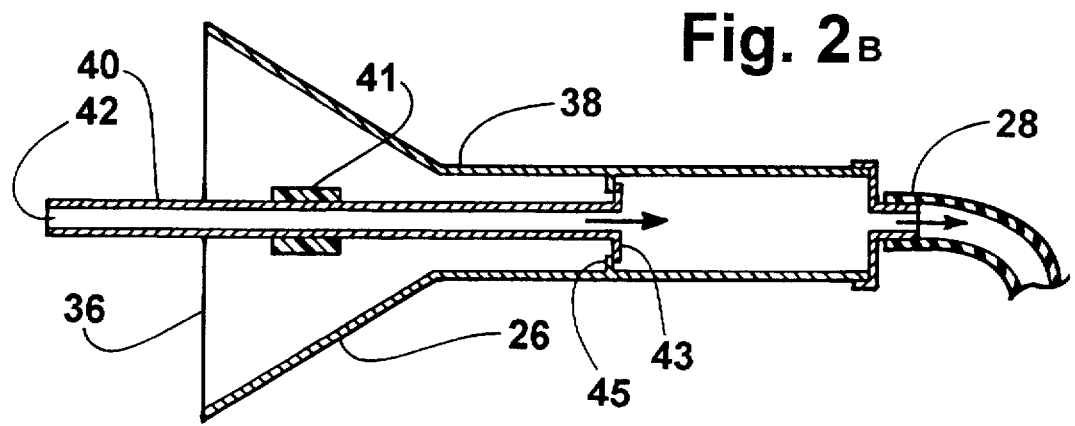
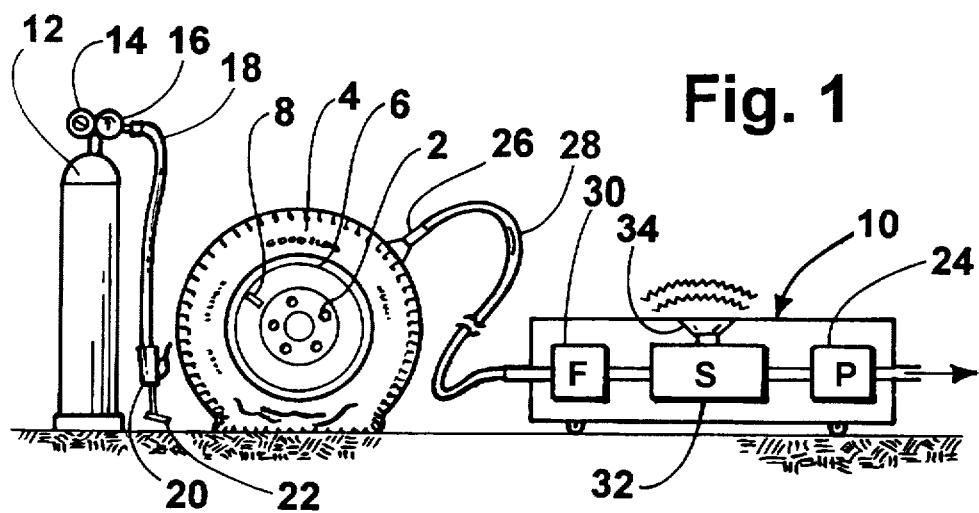

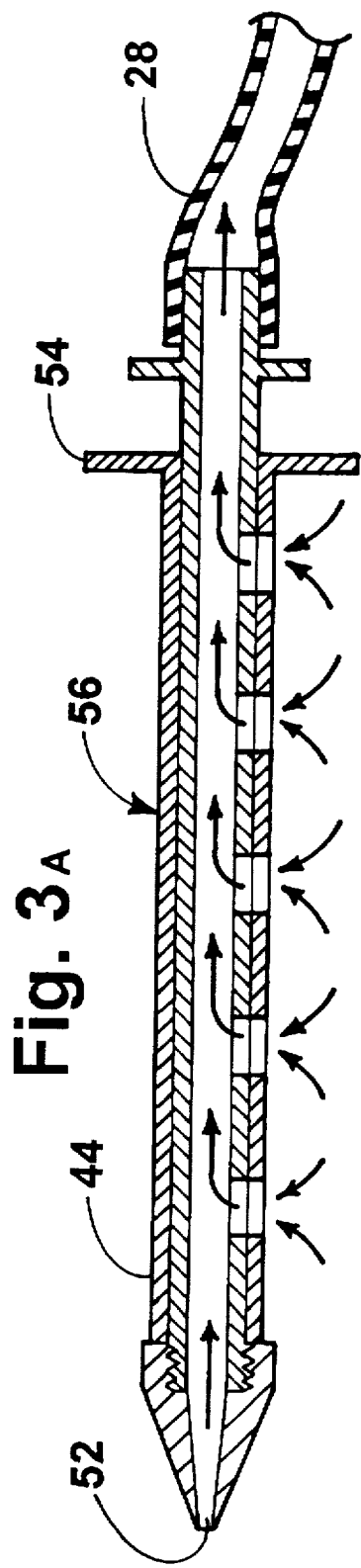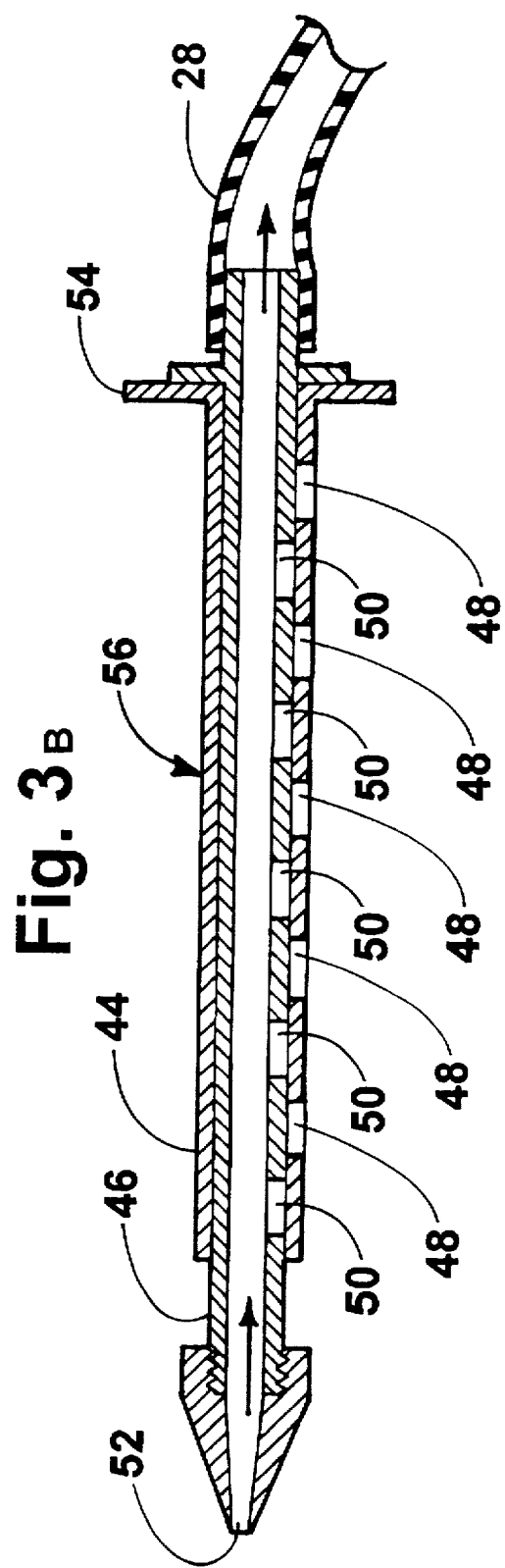

TIRE PUNCTURE LOCATOR

CROSS REFERENCE TO RELATED APPLICATIONS

Not applicable.

STATEMENT RE FEDERALLY SPONSORED RESEARCH OR DEVELOPMENT

Not applicable.

REFERENCE TO A "MICROFICHE APPENDIX"

Not applicable.

BACKGROUND OF THE INVENTION

When so much air has leaked out of a pneumatic vehicle tire that it can no longer be used for its intended purpose, the tire is said to be a flat tire. In spite of many improvements that have been made to pneumatic tires, flat tires are still a familiar occurrence.

There are several reasons why a tire may become flat. Probably the most common is punctures caused by running over nails, or shards of glass or wood. Less common causes include a leaky check valve or a defective seal between a tubeless tire and its wheel.

If the flat tire is caused by a puncture, and if the puncturing object remains embedded in the tire, it may frequently be located by visual inspection. About 40 percent of the time, the puncturing object cannot be located by visual inspection, and in these cases it is necessary to remove the wheel and tire from the vehicle to continue the search.

The most common technique used in searching for leaks is to inflate the tire with air to a higher-than-normal pressure, and to partially immerse the tire in a basin or tub of water. The location of the leak is then betrayed by the emergence of bubbles from the puncture or other defective part such as the check valve or the rim sealing bead.

This method has its limitations. The tire must be removed from the vehicle and is usually dusty, which causes the water to become murky, making the bubbles difficult to detect. If the leak is extremely slow, it may be difficult to notice the few bubbles that emerge. Also, it is difficult to carry out this type of testing without becoming wet and dusty.

After a particularly annoying flat tire, the present inventor set out to find a better way of locating leaks in pneumatic tires.

BRIEF SUMMARY OF THE INVENTION

As a result of his extensive work in the field of gas sensors, the present inventor was aware that such sensors can be very effective in detecting minute concentrations of gas. In fact, in U.S. Pat. No. 5,053,754 he describes a carbon dioxide sensor that is extremely sensitive and that can be made quite inexpensively. To avoid unnecessary repetition, the disclosure of U.S. Pat. No. 5,053,754 is incorporated herein by reference.

A small amount of carbon dioxide is always present in the atmosphere at concentrations as low as 300 parts per million and varies upward to two or three times that figure in response to environmental circumstances, such as industrial activity. Even an inexpensive carbon dioxide sensor can measure the concentration to within 10 parts per million.

Thus, it occurred to the present inventor that instead of attempting to detect the leakage of air into an atmosphere of air it would make better sense to detect a leakage of carbon dioxide into an atmosphere of air.

In accordance with the present invention, the partially flat tire is inflated with gaseous carbon dioxide from a pressurized source so that the concentration of carbon dioxide gas within the tire becomes extremely high, typically 200,000 to 400,000 parts per million of carbon dioxide. With that great a concentration of carbon dioxide emerging from the defective area, it is quite easy to detect the emerging carbon dioxide in an atmosphere of air, using the type of carbon dioxide sensor described in U.S. Pat. No. 5,053,754. By continuously sampling from a small region adjacent the surface of the tire, the location of the leak can readily be found.

In a preferred embodiment of the present invention, the process of determining the location of the leaking carbon dioxide is made easier through the use of a hand-held gas collector having a special design that permits it to first sample a narrow elongated region of the tire across the tread (bottom surface of tire) as the tire is being rotated. After the leak is identified to be in the narrow elongated region of the tire at a particular rotation position, the hand-held gas collector is modified to one that could pin point exactly the location of the leak along the narrow elongated region so identified.

The novel features which are believed to be characteristic of the invention, both as to its components and its method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE SEVERAL VIEWS OF THE DRAWING

FIG. 1 is a diagram showing the components of the tire puncture locator of the present invention in a preferred embodiment;

FIG. 2 is a cross sectional side view of a first preferred embodiment of a hand-held sample gas collector to be used with the present invention. FIG. 2A shows a position of the hand-held sample gas collector to be used for scanning a large and elongated area of the tire across the tread and FIG. 2B shows a position used for pin-pointing a smaller area for locating the exact position of the leak; and, FIG. 3 is a cross sectional view of a second preferred embodiment of a hand-held sample gas collector to be used with the present invention. FIG. 3A shows a position of the hand-held sample gas collector to be used for scanning a large and elongated area of the tire across the tread and FIG. 3B shows a position used for pin-pointing a smaller area for locating the exact position of the leak.

DETAILED DESCRIPTION OF THE INVENTION

Typically a tire 4 becomes flat while mounted on a wheel 6 which is attached to the vehicle by nuts, of which the nut 2 is typical. A check valve 8 extends through a hole in the metal wheel 6 to permit air to be injected into the tire.

The present invention includes a gas sampling system 10 and a source 12 of pressurized carbon dioxide gas. In the preferred embodiment, the source 12 is a metal cylinder containing carbon dioxide gas under pressure. The gas is released from the cylinder by opening the valve 14 which also reduces the pressure of the outflowing gas through a throttling effect. The pressure at which the gas is supplied is displayed on the gauge 16. The carbon dioxide is supplied through a flexible hose 18 that terminates at a hand-operated valve 20 that includes a fixture 22 that is sized and shaped to sealingly engage the check valve 8 that extends from the wheel 6. The hose 18, the hand-operated valve 20, and the fixture 22 are of a type commonly used at gas stations for injecting air into tires.

In accordance with the present invention, the fixture 22 is held by hand onto the check valve 8, while carbon dioxide gas is injected into the tire 4 under control of the hand-operated valve 20.

Initially the pressure in the flat tire would ordinarily be substantially less than 20 psig. In an optional step, the user may choose to let some of the remaining air out of the flat tire, to reduce dilution of the carbon dioxide, which is then injected into the tire until the tire pressure exceeds 20 psig and is typically in the range of 25 to 30 psig. Accordingly, after the inflation with carbon dioxide, the concentration of carbon dioxide in the tire will ordinarily exceed 200,000 parts per million; any gas that leaks from the tire will initially have that concentration. Even if the leaked gas is diluted by the ambient air by a factor of 100, its concentration should still be on the order of 2,000 parts per million, which is extremely easy to detect using the gas sampling system 10.

In a preferred embodiment, the gas sampling system 10 includes a suction pump 24 that continually draws gas in through a hand-held collector 26, through a flexible hose 28, through an in-line air filter 30, and through a carbon dioxide sensor 32. The carbon dioxide sensor 32 continually measures the concentration of carbon dioxide in the sample stream, and produces an electrical signal representative of the concentration. In the preferred embodiment, this electrical signal is constantly compared with a preset voltage representative of approximately 10,000 ppm of carbon dioxide concentration. When the measured concentration of carbon dioxide exceeds about 10,000 ppm, an audio tone is emitted by the loudspeaker 34, otherwise there is no tone sound. In an alternative embodiment, this electrical signal is applied to control the loudness of a tone emitted by loudspeaker 34. In yet another alternative embodiment, the electrical signal may be used to alter the pitch of a tone emitted by the loudspeaker 34 in relation to the concentration of carbon dioxide in the sample stream.

FIGS. 2A and 2B show the form of the collector used in a preferred embodiment of the invention. Referring to FIG. 2A, the collector 26 includes a narrow elongated opening 36 through which gas is drawn into the collector 26 and from there into the flexible hose 28. The collector 26 also includes a small tube 40 whose opening 42 is flush with the elongated opening so that gas is also drawn through tube 40 into flexible hose 28. The length of the opening 36 is at least 4 inches. Ordinarily, the user would first sweep the collector as shown in FIG. 2A around the circumference of the tire, maintaining the opening 36 adjacent to the surface of the tire, and holding the collector by the handle 38 so as to maintain the longer dimension of the opening 36 oriented across the tread. Note that the elongated shape of the opening 36 permits the surface of the tire to be swept much more rapidly than if only a smaller, more circular collector were used.

If the leak is found at the location of the collector by virtue of the loudspeaker 34 emitting a sound tone, such a leak location could be more precisely determined by slidably advancing the smaller tube 40 beyond the elongated opening 36 of the gas collector 26 and using it to pin-point the exact location of the leak, as depicted in FIG. 2B. In this configuration the flange 43 of the tube 40 blocks the flow of gas through the hole in the partition 45. Friction between the bushing 41 and the tubing 40 holds the tubing in the positions shown in FIGS. 2A and 2B.

If the sweeping of the large elongated opening 36 of the gas collector (see FIG. 2A) around the tread of the tire does not result in detection of the leak, the user can next sweep the collector 26 around the side walls of the tire. It is noteworthy that the apparatus of the present invention detects not only leakage through punctures in the tire, but also can detect leakage through a defective check valve or through a defective seal between the tire and the wheel.

FIGS. 3A and 3B show an alternative embodiment for the gas sample collector. The collector 56 comprises a tube 46 and a sleeve 44. The side walls of the sleeve 44 and the tube 46 contain rows, 48 and 50 respectively, of apertures for drawing a gas sample through the flexible hose 28 into the carbon dioxide sensor 32 of FIG. 1. The collector 56 further contains a small opening 52 at the collecting end of the tube 46 for drawing a gas sample from a small area surrounding the small opening. The sleeve 44 can be slid along the tube 46 (thereby covering up the side apertures of the latter) by drawing a sliding knob 54 backwards as depicted in FIG. 3B. When the sliding knob 54 is in the position of FIG. 3B, the gas collector 56 can draw gas only through opening 52 to enable pin-pointing of the exact position of a leak. Alternatively, when the sliding knob 54 is in a forward position as depicted in FIG. 3A, the gas collector 56 draws the gas sample from all the side apertures 48 and 50, which are then in registration, as well as from opening 52. In an alternative embodiment requiring a circular tube 46 and a circular sleeve 44, instead of being slid lengthwise along the tube 46, the sleeve 44 is merely rotated about the tube 46 to an angle where the holes 50 of the tube 46 are covered by the sleeve 44.

Because carbon dioxide is practically an inert gas, its use in conformity with the present invention is safe and non-polluting.

Thus, there has been described an apparatus for detecting leaks in pneumatic tires. The apparatus includes a source of pressurized carbon dioxide that is used to re-inflate the tire with carbon dioxide, so that a strong concentration of carbon dioxide gas will be present in any gas that leaks out of the tire. This enhanced concentration of carbon dioxide gas is detected by a gas sampling system that includes an audible alarm that alerts the user when the location of the leak has been found.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. Apparatus for determining the location of a leak in a tire comprising:
    a source of pressurized carbon dioxide gas for use in injecting a quantity of carbon dioxide gas into the tire;
    a gas sampling system for continuously measuring the concentration of carbon dioxide in an inflowing gas stream, said gas sampling system including
        collector means for drawing the gas stream from selected locations adjacent the surface of the tire;

sensor means for producing an electrical signal representative of the instantaneous concentration of carbon dioxide in the gas stream; and, alarm means responsive to said electrical signal for producing an audible alarm related to the instantaneous concentration of carbon dioxide.

2. The apparatus of claim 1 wherein said collector is manually moved along the tire.

3. The apparatus of claim 1 wherein the tire is moved with respect to said collector means.

4. The apparatus of claim 1 wherein said audible alarm changes its loudness in relation to the instantaneous concentration of carbon dioxide.

5. The apparatus of claim 1 wherein said audible alarm changes its pitch in relation to the instantaneous concentration of carbon dioxide.

6. The apparatus of claim 1 wherein said audible alarm is generated only when the instantaneous concentration of carbon dioxide exceeds a preset value.

7. A method for determining the location of a leak in a tire of a vehicle, comprising the steps of:

injecting pressurized carbon dioxide gas into the tire to increase the concentration of carbon dioxide within the tire to render the concentration of carbon dioxide within the tire many times greater than the concentration of carbon dioxide in the atmosphere;

sampling the gas surrounding the tire at selected locations adjacent the surface of the tire;

drawing each gas sample through a carbon dioxide sensor that identifies those samples that contain an extraordinarily high concentration of carbon dioxide;

noting the locations from which the samples containing an extraordinarily high concentration of carbon dioxide were drawn.

8. The method of claim 7 wherein the injecting, sampling, drawing, and noting steps are performed without removing the tire from the vehicle.

* * * * *